(12) United States Patent
Nakamura et al.

(10) Patent No.: US 6,235,188 B1
(45) Date of Patent: May 22, 2001

(54) WATER POLLUTION EVALUATING SYSTEM WITH ELECTROLYZER

(75) Inventors: Shinichi Nakamura, Osaka; Kunihiko Fukuzuka, Habikino; Katsuhiro Misawa, Osaka; Akushige Okuda, Habikino, all of (JP)

(73) Assignee: Omega Co., Ltd. (JP)

(*) Notice: Subject to any disclaimer, the term of this patent is extended or adjusted under 35 U.S.C. 154(b) by 0 days.

(21) Appl. No.: 09/306,599

(22) Filed: May 6, 1999

(30) Foreign Application Priority Data

Jul. 23, 1998 (JP) .................................................. 10-223702

(51) Int. Cl.[7] ...................................................... C02F 1/461
(52) U.S. Cl. ........................ 205/742; 205/779.5; 204/237; 210/243; 210/748; 210/85; 210/192; 210/169
(58) Field of Search ..................................... 210/746, 96.1, 210/96.2, 85, 243, 192, 169, 748; 205/742, 743, 744, 778.5, 556, 779.5, 687; 204/435, 240, 232, 237, 228.6, 236

(56) References Cited

U.S. PATENT DOCUMENTS

| | | | |
|---|---|---|---|
| 3,839,162 | * | 10/1974 | Ammer . |
| 3,862,895 | * | 1/1975 | King et al. . |
| 3,930,798 | * | 1/1976 | Schierjott et al. . |
| 3,935,092 | * | 1/1976 | Bizot et al. . |
| 3,956,094 | * | 5/1976 | Capuano . |
| 4,767,511 | * | 8/1988 | Aragon . |
| 5,560,246 | * | 10/1996 | Bottinger et al. . |
| 5,843,291 | * | 12/1998 | Eki et al. . |

FOREIGN PATENT DOCUMENTS

| | | |
|---|---|---|
| 3-235048 | 10/1991 | (JP) . |
| 9-15200 | 1/1997 | (JP) . |

* cited by examiner

Primary Examiner—Joseph W. Drodge
Assistant Examiner—Terry K. Cecil
(74) Attorney, Agent, or Firm—Hayes, Soloway, Hennessey, Grossman & Hage

(57) ABSTRACT

When the water stored in a reservoir 1 and containing chlorine ion and/or bromine ion is supplied to and circulated through an electrolyzer 4 and electrolyzed therein to create hypochlorous acid and/or hypobromous acid so that the water is purified and sterilized, a potential difference measuring unit is interposed between a measuring electrode dipped into the water containing the hypochlorous acid and/or hypobromous acid and a reference electrode dipped into water having a prescribed electric conductivity and containing neither hypochlorous acid nor hypobromous acid to thereby evaluate a measured potential difference as a COD value which is an index of pollution. With this arrangement, a polluted state of water can be promptly and simply evaluated as the COD value.

16 Claims, 11 Drawing Sheets

(a)

(b)

WATER POLLUTION EVALUATING SYSTEM WITH ELECTROLYZER

BACKGROUND OF THE INVENTION

1. Field of the Invention

The present invention relates to a water pollution evaluating system for evaluating the pollution of water stored in a reservoir such as a pool, bath, cooling tower, fish raising vessel and the like.

2. Description of the Related Art

As a method of evaluating the pollution of water stored in a reservoir such as a pool, bath, cooling tower, fish raising vessel and the like, a COD component which is mainly water soluble organic matters in water has been measured and the pollution of the water has been evaluated by the increase or decrease of the COD value thereof.

Recently, it has been recognized that it is important to manage and regulate the water stored in the reservoir such as the pool, bath, cooling tower, fish raising vessel and the like so that the water is maintained in a clean state. Thus, attention has been paid to a method of sterilizing and purifying water using hypohalogenous acid having a sterilizing and purifying capability which is slightly contained in the water or produced by electrolyzing the water by adding a suitable amount of chlorine ion or bromine ion to the water.

In the water stored in the reservoir such as the pool, bath, cooling tower, fish raising vessel and the like, when the concentration of the hypohalogenous acid produced by electrolysis is higher than a suitable concentration, it may aversely affect human bodies, raised fishes, equipment and the like which are in contact with the water and rough skin, death, corrosion and the like may be caused thereto by the hypohalogenous acid; whereas when the concentration of the hypohalogenous acid produced by the electrolysis is not sufficient, there arises a problem that the water is not sufficiently sterilized and purified so that a water passage is clogged by the occurrence of diseases, waterweeds and the like and a heat efficiency is lowered. Accordingly, the production of the hypohalogenous acid must be properly controlled in accordance with a degree of pollution of water.

Incidentally, as a method of measuring the COD as an index of the pollution of waters there has been employed a method wherein a portion of water to be measured is collected in a suitable amount; potassium permanganate is added to the water as an oxidizing agent under prescribed conditions; the amount of the potassium permanganate consumed to oxidize a COD component is measured by titration; and the pollution of the water is calculated by converting the amount of consumed potassium permanganate into the amount of oxygen. In the conventional method, however, not only is a long time required to take the measurement but also the measurement is complex because the water must be collected as necessary and the above procedure must be carried out. Accordingly, there has been desired a system capable of promptly and simply evaluating a COD value as an index of the pollution of water in an apparatus in order to control the production of the hypohalogenous acid as described above.

An object of the present invention made in view of the above problem is to provide a water pollution evaluating system capable of promptly and simply evaluating the polluted state of water as a COD value.

SUMMARY OF THE INVENTION

To solve the above problem, a water pollution evaluating system of the present invention has a feature wherein it comprises an electrolyzer for electrolyzing water, which is stored in a reservoir such as a pool, bath, cooling tower, fish raising vessel, etc., contains chlorine ion and/or bromine ion and is supplied to the electrolyzer and circulated therethrough, and creating hypochlorous acid and/or hypobromous acid to sterilize and purify the water; a measuring electrode dipped into the water containing the hypochlorous acid and/or the hypobromous acid; a reference electrode dipped into water having a prescribed electric conductivity and containing neither hypochlorous acid nor hypobromous acid; and a potential difference measuring unit interposed between the reference electrode and the reference electrode for measuring the potential difference between the waters, wherein the measured potential difference is evaluated as a COD value as an index of pollution.

(a) According to the above feature, there is established such a correlation that when the COD component as the polluted component in the water increases, the hypochlorous acid and hypobromous acid produced in the electrolyzer to sterilize and purify the COD component is consumed and the potential difference caused between the respective electrodes drops, whereas when the COD component as the polluted component in the water decreases, the hypochlorous acid and hypobromous acid are not consumed and the potential difference caused between the respective electrodes increases. Accordingly, the measurement of the potential difference permits the COD value of the water at the time to be simply evaluated at an almost real time In the water pollution evaluating system of the present invention, it is preferable that the reference electrode is dipped into the same water as that into which the measuring electrode is dipped except that the hypochlorous acid and/or hypobromous acid contained in the water into which the reference electrode is dipped is almost perfectly decomposed.

(b) With this arrangement, since the difference between the water into which the reference electrode is dipped and the water into which the measuring electrode is dipped resides only in the concentration of the hypochlorous acid and/or the hypobromous acid and the waters contain almost the same other electrolyte components, the potential difference resulting from the difference of concentrations of the other electrolyte components can be almost eliminated. Therefore, the potential difference based on the difference of the concentrations of the hypochlorous acid and/or the hypobromous acid can be correctly measured.

It is preferable that the water pollution evaluating system of the present invention further comprises a conversion unit for converting the potential difference into a pollution level set to a prescribed grade or a COD value; and an output unit for outputting the converted pollution level or the COD value.

(c) With this arrangement, since the pollution level or the COD value based on the potential difference is automatically converted by the conversion unit and output, the pollution level or the COD value of the water at the time can be directly confirmed when necessary.

It is preferable that the water pollution evaluating system of the present invention further comprises an auxiliary flow area which is branched from the main flow passage of the circulating water and through which a portion of the water passes in an approximately constant flow rate, wherein at least the reference electrode is disposed to the auxiliary flow area.

(d) With this arrangement, since the water flows through the auxiliary flow area in an approximately constant flow rate regardless of the fluctuation of the flow rate of the water in the main flow passage caused by the respective states of sterilization and purification, the change of the measured potential difference due to the fluctuation of the flow rate is reduced. Accordingly, the potential difference can stably be measured regardless of the state of the main flow passage.

It is preferable that the water pollution evaluating system of the present invention further comprises a time measuring unit for starting the measurement of time when the electrolysis carried out by the electrolyzer is interrupted, wherein the potential difference is measured when a preset time elapses from the start of the measurement of the time.

(e) With this arrangement, the effect of the charge accumulated in the water by the electrolysis on the measured potential difference can be reduced, whereby the potential difference can be more correctly measured.

It is preferable that the water pollution evaluating system of the present invention further comprises a reference electrode chamber surrounding the reference electrode and communicating with the water; and a membrane-like decomposing unit such as a membrane carrying a catalyst, activated carbon, etc. capable of decomposing hypochlorous acid and hypobromous acid, an ion exchange membrane or the like disposed to close the reference electrode chamber.

(f) With this arrangement, since not only the interior of the reference electrode chamber can be simply made to a state in which neither hypochlorous acid nor hypobromous acid exists by the use of the membrane-like decomposing unit but also the reference electrode chamber can be closed by the decomposing means, only the hypochlorous acid and hypobromous acid which intend to invade into the reference electrode chamber is decomposed. Accordingly, the amount of hypochlorous acid and hypobromous acid to be decomposed by the decomposing unit can be reduced, whereby the life of the decomposing unit can be prolonged.

In the water pollution evaluating system of the present invention, it is preferable that the interior of the reference electrode chamber is filled with water containing potassium ion having a prescribed concentration.

(g) With this arrangement, since potassium ion exists in the reference electrode chamber and the moving speed of the potassium ion is higher than that of other alkaline ions such as sodium ion, lithium ion, etc., the potassium ion increases a property for following the change of the potential difference, whereby the sensitivity in the measurement of the potential difference can be increased as well as the effect of the electrolysis on the measurement of the potential difference can be promptly eliminated to thereby shorten a measuring time.

In the water pollution evaluating system of the present invention, it is preferable that the potential difference measuring means includes a leakage current preventing circuit disposed in front of an amplifier for amplifying the potential difference caused between the respective electrodes for canceling or reducing the leakage voltage from the amplifier.

(h) With this arrangement, even if hypochlorous acid or hypobromous acid of a relatively low concentration is used in the pool, bath, cooling tower, fish raising vessel and the like, the effect of the leakage current on the small potential difference caused between the electrodes can be reduced or eliminated and the potential difference is correctly amplified. Accordingly, the potential difference can be correctly measured as well as even if the concentration of the hypochlorous acid and hypobromous acid is relatively low, the COD value can be correctly evaluated.

In the water pollution evaluating system of the present invention, it is preferable that the potential difference measuring means includes a leakage current preventing circuit disposed in front of an amplifier for amplifying the potential difference caused between the respective electrodes for canceling or reducing the leakage voltage from the amplifier.

(i) With this arrangement, the concentration, flow rate and the like of the hypochlorous acid and hypobromous acid can be simply controlled based on the COD values of the water in correspondence to the respective pollution levels because the pollution levels which correspond to the COD values are outputted.

DESCRIPTION OF THE PREFERRED EMBODIMENTS

Embodiments of the present invention will be described below with reference to the accompanying drawings.
(Embodiment 1)

An embodiment 1 shows an example provided with a water pollution evaluating mechanism of the present invention applied to a 24-hour-operating bath.

Figure 1:
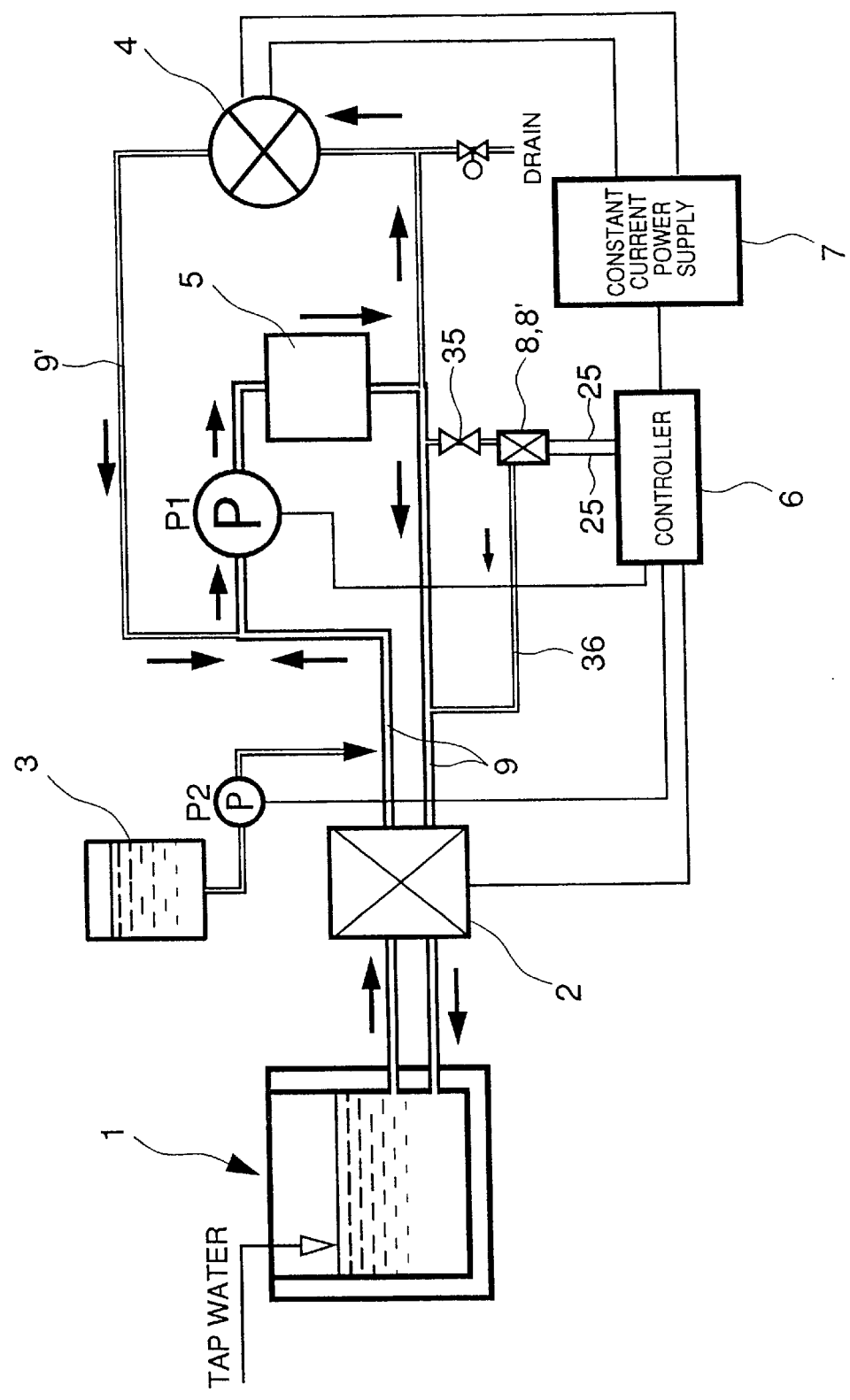
FIG. 1 is a system flow diagram showing the arrangement of a 24-hour-operating bath of an embodiment 1 of the present invention.
Figure 2:
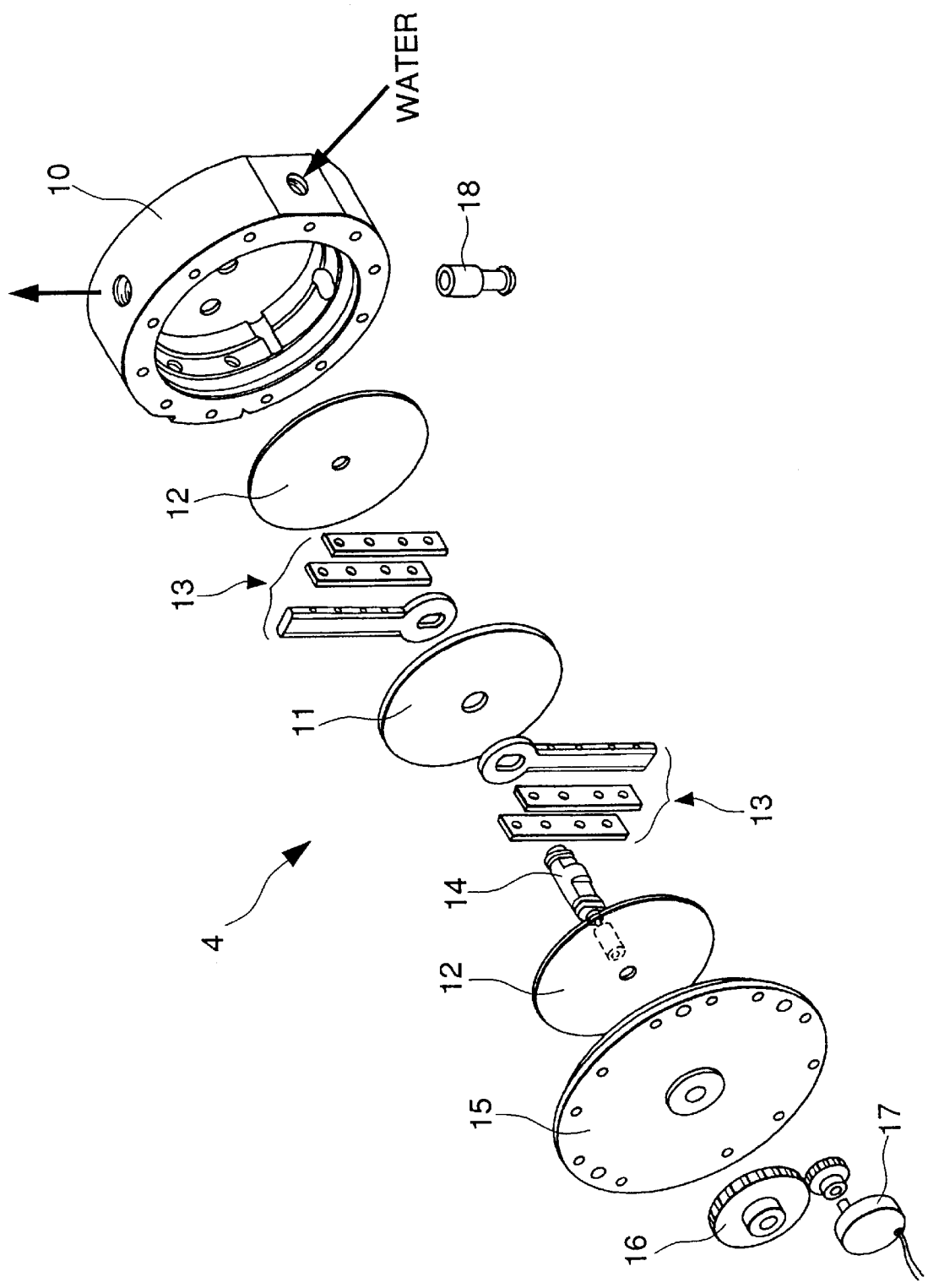
FIG. 2 is a developed perspective view showing an electrolyzer used in the 24-hour-operating bath of the embodiment 1 of the present invention.
Figure 3:
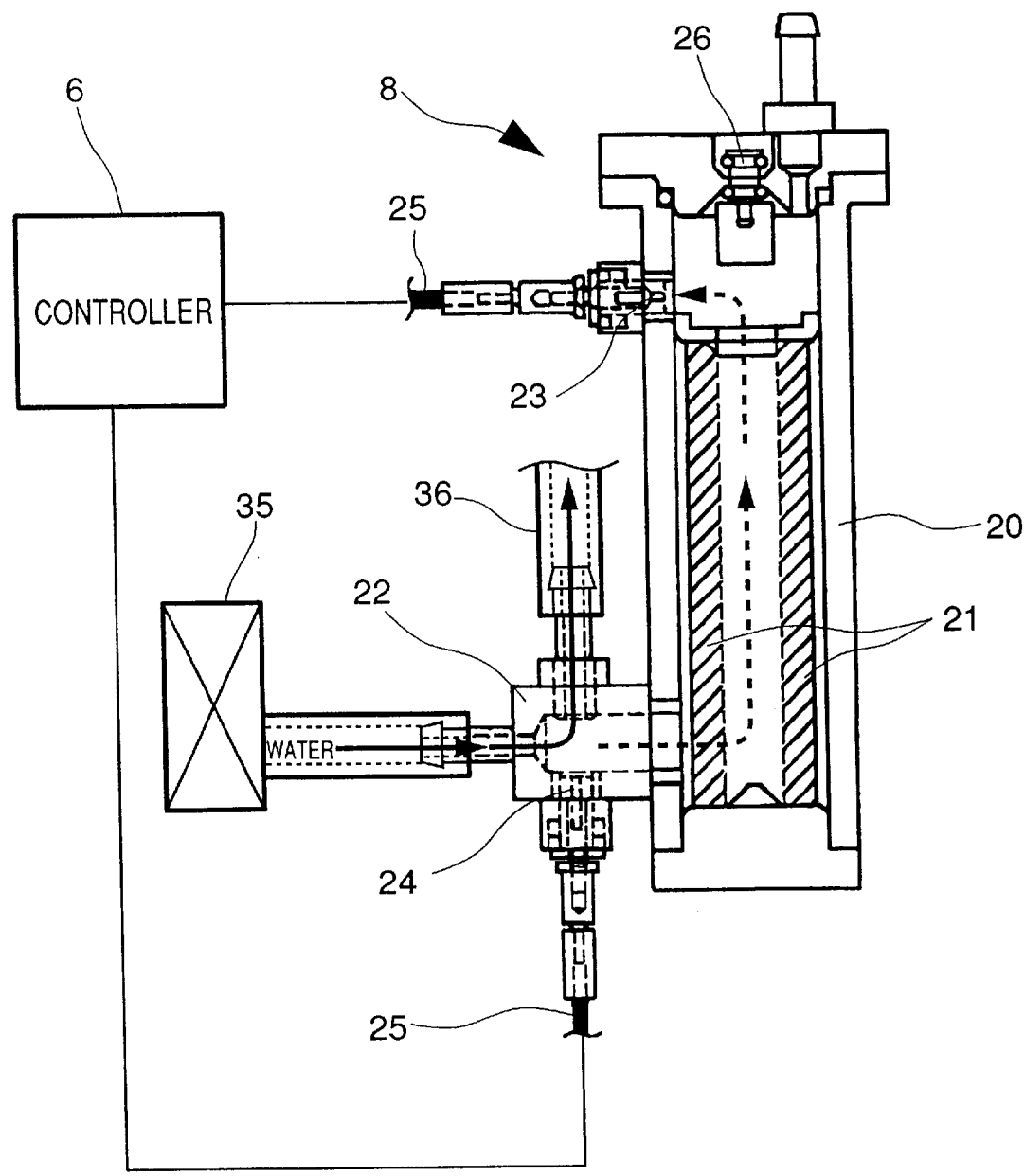
FIG. 3 is a side sectional view of a sensor unit having a water pollution evaluating mechanism of the present invention used in the 24-hour-operating bath of the embodiment 1 of the present invention.
Figure 4:
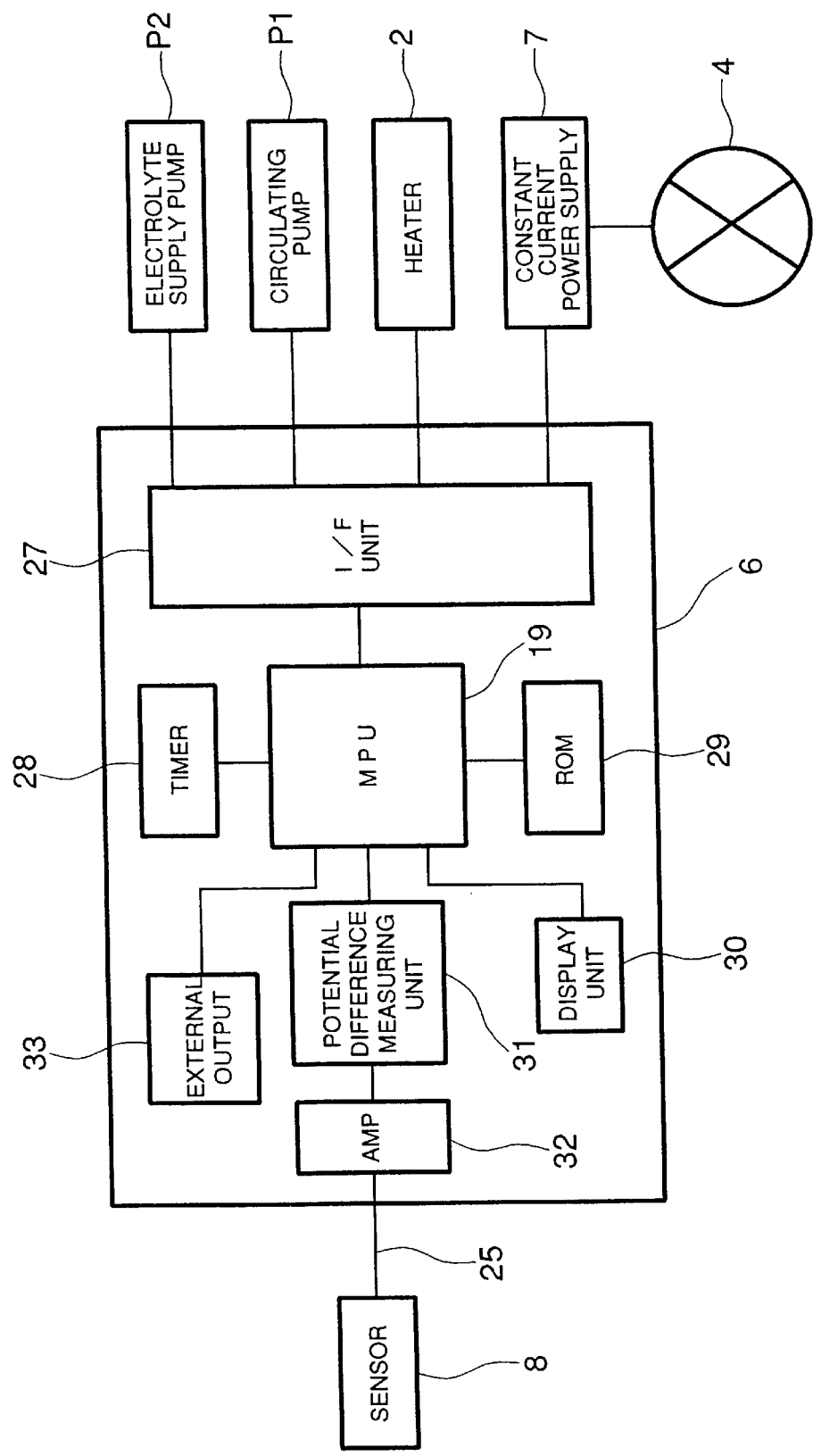
FIG. 4 is a block diagram showing the arrangement of a controller used in the 24-hour-operating bath of the embodiment 1 of the present invention and the connection of the controller to respective components.

FIG. 1 is a system flow diagram showing the arrangement of the 24-hour-operating bath of the embodiment 1, FIG. 2 is a developed perspective view showing an electrolyzer used in the 24-hour-operating bath of the embodiment 1, FIG. 3 is a side sectional view showing a sensor unit having a water pollution evaluating mechanism of the present invention used in the 24-hour-operating bath of the embodiment 1, FIG. 4 is a block diagram showing the arrangement of a controller used in the 24-hour-operating bath of the embodiment 1 and the connection of the controller to respective components, FIG. 5A is a circuit diagram showing a conventional amplifier and FIG. 5B is a circuit diagram showing an amplifier having a leakage current preventing circuit used in the embodiment 1.

The 24-hour-operating bath of the embodiment 1 has a system arranged essentially as shown in FIG. 1. In FIG. 1, numeral 1 denotes a bath including a circulation passage 9 disposed thereto for circulating the water in the bath 1. The circulation passage 9 has a circulation pump 1P for circulating the water in a prescribed flow rate, a heater 2 for heating the water to a prescribed temperature and a filter 5 for removing the foreign substances and the like in the water each disposed in the circulation passage 9 so that the water is heated to the prescribed temperature and filtered by the filter 5 while it is circulated through the circulation passage 9.

A return passage 9' is disposed to the circulation passage 9 to return the water from the downstream side of the circulating pump P1 to the upstream side thereof as well as an electrolyzer 4 is disposed in the return passage 9' to produce hypochlorous acid or hypobromous acid by electrolyzing the water passing through the return passage 9'. Thus, the water containing hypochlorous acid or hypobromous acid produced by the electrolysis returns to the circulation passage 9 as a main passage from the upstream side of the circulating pump P1 and sterilizes and purifies the water.

In the embodiment 1, since the water in the bath 1 is suitably replenished with tap water ordinarily, hypochlorous acid can be produced by the electrolysis carried out by the electrolyzer 4 because electric conductivity is provided by chlorine ion and the like contained in the tap water. However, when the electric conductivity is lowered below a prescribed value by the insufficient amount of the chlorine ion in the water and the voltage between the anode and the cathode of the electrolyzer 4 is increased above a prescribed value, salt water having a prescribed concentration, which is contained in an electrolyte bottle 3 for supplying chlorine ion to the water, is suitably supplied to the circulation passage 9 by a pump P2 so that the concentration of the chlorine ion in the water is kept to at least 5 ppm.

When the concentration of chlorine ion or bromine ion is too low, the electrolysis cannot be preferably carried out due to the decrease of the electric conductivity of the water as well as the efficiency for producing hypochlorous acid or hypobromous acid by the electrolysis is lowered. Accordingly, it is preferable that the concentration of chlorine ion is at least 5 ppm as described above.

The electrolyzer 4 used in the 24-hour-operating bath of the embodiment 1 has a structure as shown in FIG. 2. That is, a circular anode plate 11 that is composed of nickel simple ferrite having an area of 1.5 $dm^2$ (3 $dm^2$ in both the surfaces thereof) and circular cathode plates 12 that are composed of titanium and disposed on both the sides of the anode plate 11 at prescribed intervals (set to 5 mm in the embodiment 1) so as to clamp the anode plate 11 therebetween are engaged with and disposed in a bottomed circular cabinet 10 at the central portion thereof.

Rotatable scrapers 13 are interposed between the anode plate 11 and each of the cathode plates 12 and abutted against the respective surfaces of the confronting electrodes and rotate them to eliminate deposits produced on the surfaces of the electrodes by the electrolysis. The scrapers 13 are rotated by being coupled with a rotational shaft 14 which is rotated by a drive motor 17 and a drive gear 16 disposed externally of the cabinet 10.

The opening of the cabinet 10 is hermetically sealed by a lid member 15 and the water in the circulation passage 9 flows into the cabinet 10 from an inlet port formed at a position obliquely downward of the cabinet 10, is electrolyzed when it passes between the respective electrodes and discharged from an upper discharge port. Numeral 18 in FIG. 2 denotes a discharge port for discharging the insoluble deposits scraped by the scrapers 13.

A constant current power supply 7 is connected to the anode plate 11 and the cathode plates 12 of the electrolyzer 4 and adjusted to supply a prescribed constant current between the electrodes so that the electrolysis is carried out.

As shown in FIG. 1, the embodiment 1 has an auxiliary flow area 36 connected to the circulation passage 9 as a main stream section to permit a portion of the circulating water to flow into the auxiliary flow area 36. A constant flow rate orifice 35 is disposed to the auxiliary flow area 36 at the inlet thereof as well as a sensor unit 8 constituting the water pollution evaluating system of the present invention is disposed in the passage of the auxiliary flow area 36.

In the embodiment 1, a potential difference can be correctly measured because the fluctuation of it caused by the change of the flow rate of the water which arises depending upon various states such as bathing and the like is reduced by the provision of the constant flow rate orifice 35 and the formation of the auxiliary flow area 36 through which the water flows in an approximately constant flow rate as described above. However, the present invention is not limited to the above arrangement and the sensor unit 8 may be directly disposed to the circulation passage 9 as the main stream section without forming the auxiliary flow area 36.

As shown in FIG. 3, the sensor unit 8 is essentially composed of a cylindrical case 20 including therein a catalyst 21 for decomposing hypochlorous acid and hypobromous acid, a platinum measuring electrode 24 disposed to a cross-shaped port 22 so as to be exposed in the water to be measured and a platinum reference electrode 23 disposed so as to be exposed to the interior of the cylindrical case 20. The measuring electrode 24 and the reference electrode 23 are connected to a controller 6 through a measuring cable 25. In FIG. 3, numeral 26 denotes an air release valve.

Although the platinum is used as the electrode material of the measuring electrode 24 and the reference electrode 23 in the embodiment 1 as described above, the present invention is not limited thereto and gold, silver, carbon, etc., for example, are exemplified as other electrode materials and they can be suitably selected from the viewpoint of corrosion resistance, durability and the like so long as both the electrodes are made of the same electrode material.

Although nickel oxide is used as the catalyst 21 in the embodiment 1, the present invention is not limited thereto and any material may be used as the catalyst so long as it effectively decomposes hypochlorous acid and hypobromous acid. Thus, the oxide of iron, cobalt, titanium, manganese, etc. and activated carbon, etc. are exemplified as the catalyst and can be suitably selected from the viewpoint of life and durability.

The operation of the sensor unit 8 will be described with reference to FIG. 3. First, the space in the cylindrical case 20 is filled with the water which flows through the auxiliary flow area 36 in the approximately constant flow rate.

The hypochlorous acid or the hypobromous acid contained in the water flowing into the cylindrical case 20 is almost perfectly decomposed by the catalyst 21 so that the water in the cylindrical case 20 is maintained in a state that it contains almost no hypochlorous acid or hypobromous acid.

The measuring electrode 24 is exposed to the water which flows through the auxiliary flow area 36 in the approximately constant flow rate and neither hypochlorous acid nor hypobromous acid exists in the water to which the reference electrode 23 is exposed as described above. Accordingly, when hypochlorous acid or hypobromous acid is contained in the water, the difference of the concentrations of the hypochlorous acid or hypobromous acid appears across both the electrodes 23, 24 as a potential difference which approximately proportional to the difference of the concentrations and the potential difference can be measured by the controller 6 through the measuring cable 25.

Since the same water as the water into which the measuring electrode 24 is dipped is used as the water contained in the cylindrical case 20 having the reference electrode 23 exposed thereto and dipped thereinto and hypohalogenous (chlorous) acid is eliminated from the water by decomposing it with the catalyst 21, the components other than the hypohalogenous (chlorous) acid in the water contained in the cylindrical case 20 and those in the water into which the measuring electrode 24 is dipped can be made almost the same by using the same water. Therefore, the effect of the difference of the concentrations of the electrolytes and the like on the measurement of the potential difference can be greatly reduced because there is no difference of the concentrations of the electrolytes and the like contained in the waters located in the vicinities of the respective electrodes. Although this is preferable because only the potential difference due to the difference of the concentrations of hypohalogenous (chlorous) acid can be measured, the present invention is not limited thereto and a potential difference may be measured by disposing the reference electrode 23 in water which has a prescribed electric conductivity and does not contain the hypohalogenous (chlorous) acid.

As shown in FIG. 4, an amplifier 32 connected to the measuring cable 25 for amplifying the potential difference caused between the measuring electrode 24 and the reference electrode 23 and a potential difference measuring unit 31 for measuring the amplified potential difference are disposed in the controller 6. The potential difference measuring unit 31 is composed of an A/D converter in the embodiment 1 and digital data is output based on the measured potential difference.

The amplifier 32 used in the embodiment 1 in place of the conventional amplifier 32' shown in FIG. 5A has the circuit arrangement shown in FIG. 5B. That is, the amplifier 32 has a leakage current preventing circuit unit 34 disposed therein in front of an amplifying field effect transistor FET used as an amplifying operational amplifier. The leakage current preventing circuit unit 34 has P- and N-channel J-FETs disposed therein and connected to each other to cancel the leakage current Ig of the gate current of the field effect transistor FET.

With the above circuit arrangement, the leakage voltage Io of the sensor unit 8 to the measuring electrode can be made to almost zero because the leakage current Ig from the amplifying field effect amplifier FET is returned by the P- and N-channel J-FETs and canceled. Thus, the measurement of the potential difference is not affected by the leakage voltage.

In the embodiment 1, the field effect transistor FET is preferably used as the operational amplifier as described above because it can lower the leakage voltage thereof as compared with an ordinary transistor using a base current. However, the present invention is not limited thereto and the ordinary transistor having a large leakage voltage may be used because the leakage voltage can be reduced or canceled by the use of the leakage current preventing circuit unit 34.

As shown in FIG. 4, the potential difference data made to digital data by the potential difference measuring unit 31 is outputted to a microprocessing unit (MPU) 19 in the controller and a pollution level or a COD value corresponding to the potential difference is compared with a pollution level or a potential difference corresponding to a potential difference within a prescribed range which is preset to or prestored in a ROM 29 and converted based on the correlative database of the COD value and displayed on a display unit 30 as well as prescribed signals based on the respective pollution levels are outputted to an external output 33.

In the embodiment 1, it is determined that a measured potential less than 0 mV is a pollution level HH, a measured potential from 0 to 320 mV is a pollution level H, a measured potential from 320 to 600 mV is a pollution level L and a measured potential greater than 600 mV is a pollution level LL. The operation of the constant current power supply 7 to which the controller 6 is connected is controlled bases upon the above respective pollution levels so that the production of hypochlorous acid is controlled in the electrolyzer 4.

In the embodiment 1, when the pollution level is LL and the polluted state of the water is very low, the power supply to the electrolyzer 4 is interrupted to prevent the excessive increase of the concentration of the hypochlorous acid.

Since the respective pollution levels are outputted to the external output 33, a plurality of apparatuses which are operated in association with each other can be controlled based on the respective pollution levels. Although this arrangement is preferable because the apparatuses can be simply controlled in association with each other, the present invention is not limited thereto.

Further, a timer 28 as a time measuring unit capable of outputting time information is disposed in the controller 6. The timer 28 permits the potential difference to be measured after a prescribed time preset and stored in the ROM 29 elapses from the completion of the electrolysis performed by the electrolyzer 4.

The preset time is a time during which the effect of the charge accumulated in the water by the electrolysis on the measurement of the potential difference is almost eliminated and may be suitably determined in respective apparatuses by monitoring the change of the potential difference from the completion of the electrolysis.

Figure 6:
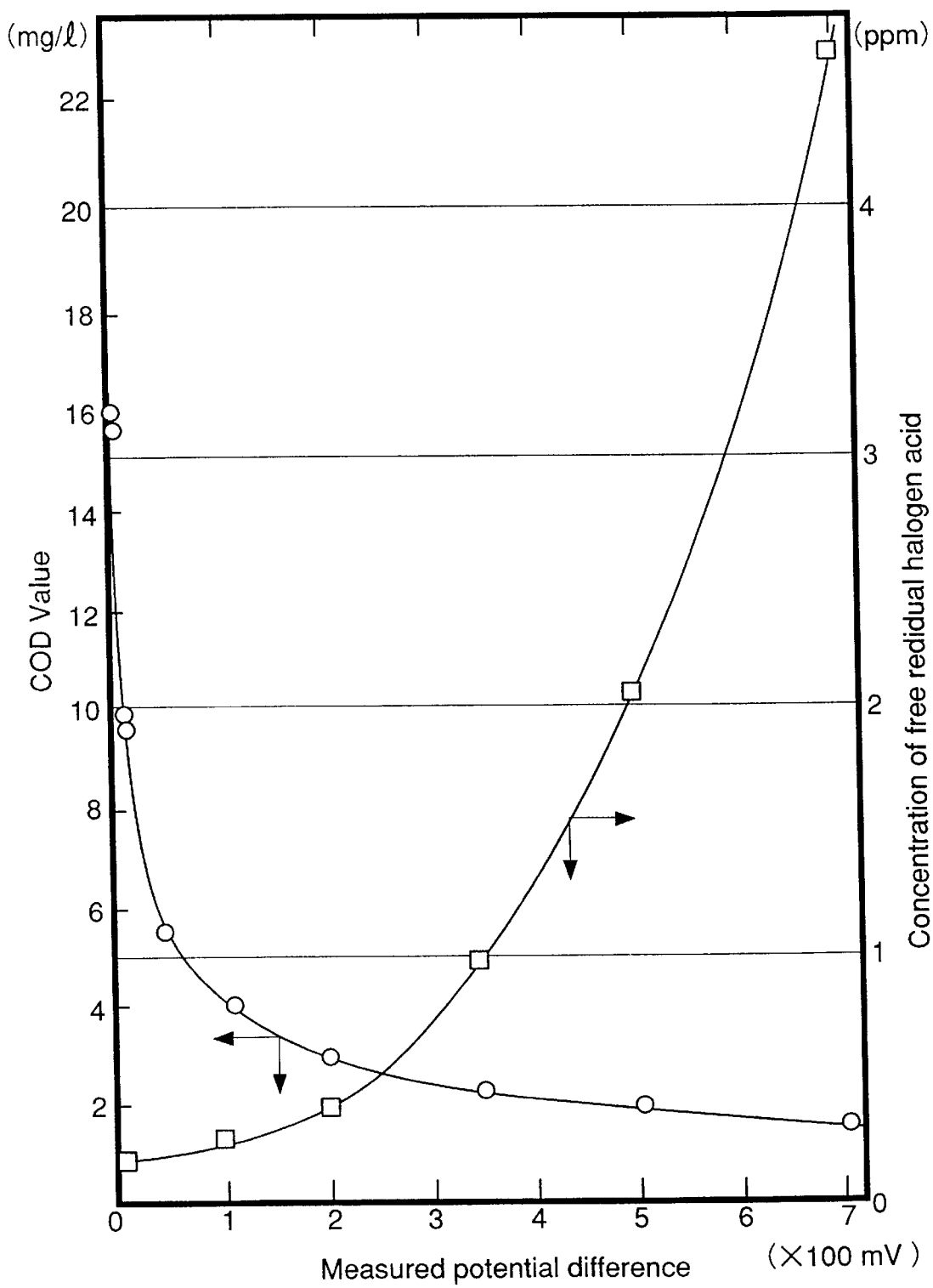
FIG. 6 is a graph showing the relationship among a COD value and a free residual halogen acid concentration at the sensor unit of the embodiment 1 of the present invention and a measured potential.

In the embodiment 1, the respective components constituting the 24-hour-operating bath are connected to the controller 6 as shown in FIG. 6 and the MPU 19 controls them through an interface (I/F) unit 27 based on a control program prestored in the ROM 29.

FIG. 6 shows the result of measurement of the relationship among the potential difference caused between the measuring electrode 24 and the reference electrode 23, the COD value of water and the concentration of free residual halogen (chloric) acid when bathing is suitably taken in the 24-hour-operating bath of the embodiment 1.

As shown in FIG. 6, the measured potential difference increases approximately in proportion to the concentration of the free hypohalogenous (chlorous) acid contained in the water. When the water is polluted by the increase of the COD component which is indicative of the pollution of the water, the free hypohalogenous (chlorous) acid is consumed to oxidize and decompose the COD component its concentration is lowered and accordingly the measured potential difference is also lowered. More specifically, when the water is sterilized and purified and less polluted, the free hypohalogenous (chlorous) acid is not consumed and its concentration is increased and accordingly the measured potential difference is also increased. As a result, since a correlation is established between the measured potential difference and the COD value as the index of the pollution of the water, the COD value as the index of the pollution of any arbitrary water can be determined by measuring the potential difference of the water. The measured potential difference can be converted into the COD value corresponding to it by storing the correlation data between the COD value and the measured potential difference in the ROM 29.

Figure 5:
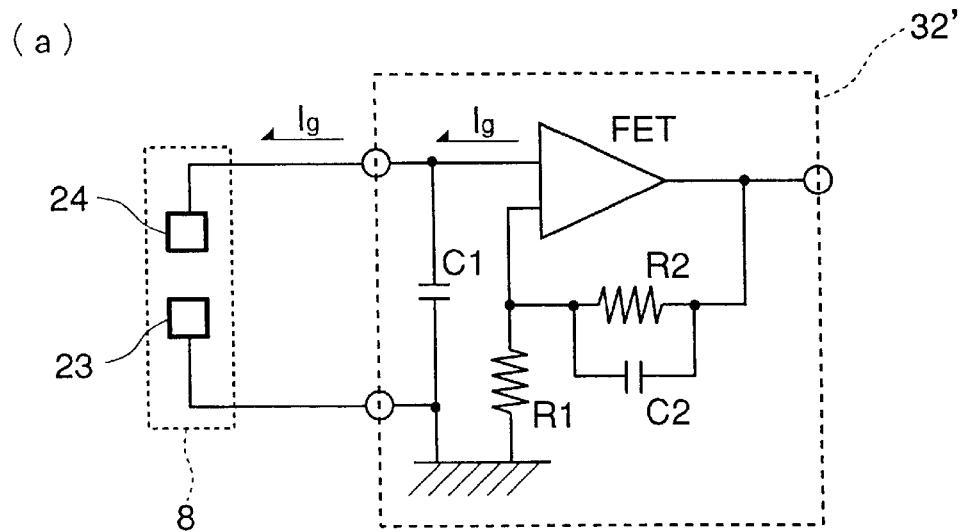
FIG. 5A is a circuit diagram showing a conventional amplifier.
FIG. 5B is a circuit diagram showing an amplifier having a leakage current preventing circuit used in the 24-hour-operating bath of the embodiment 1 of the present invention.
Figure 5:
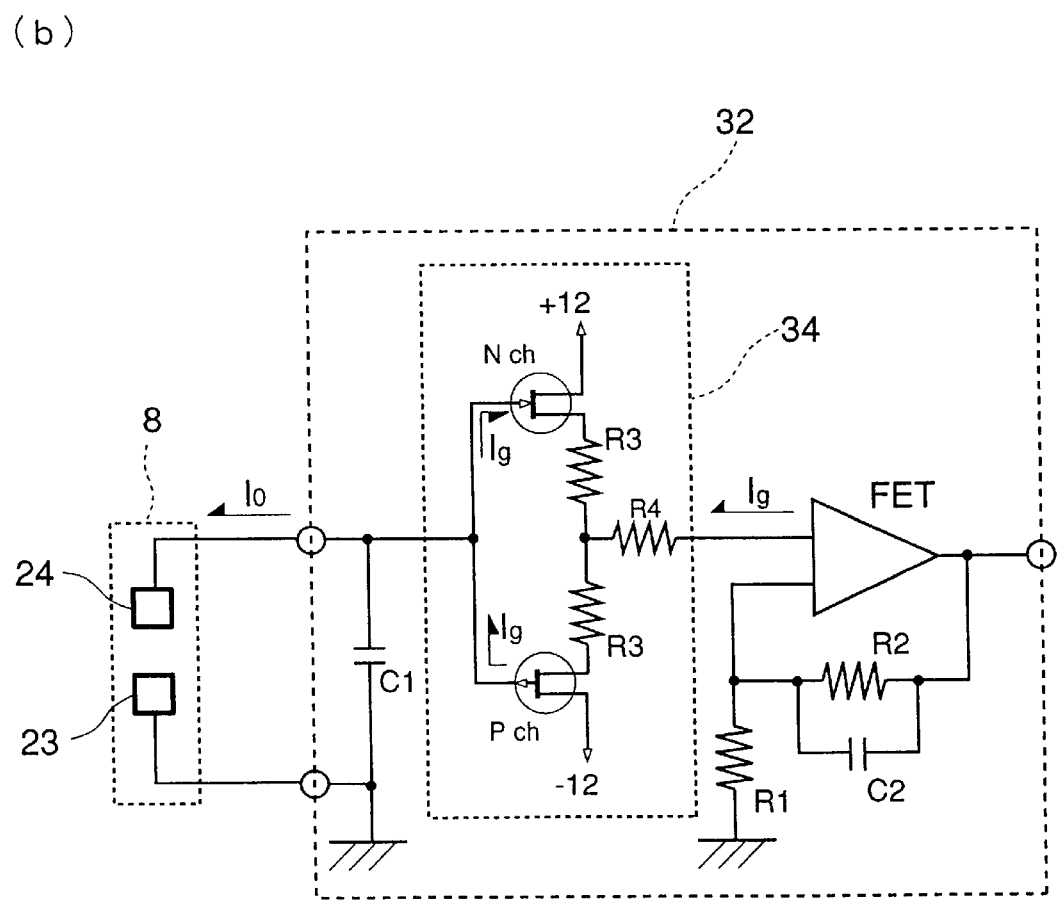
Figure 7:
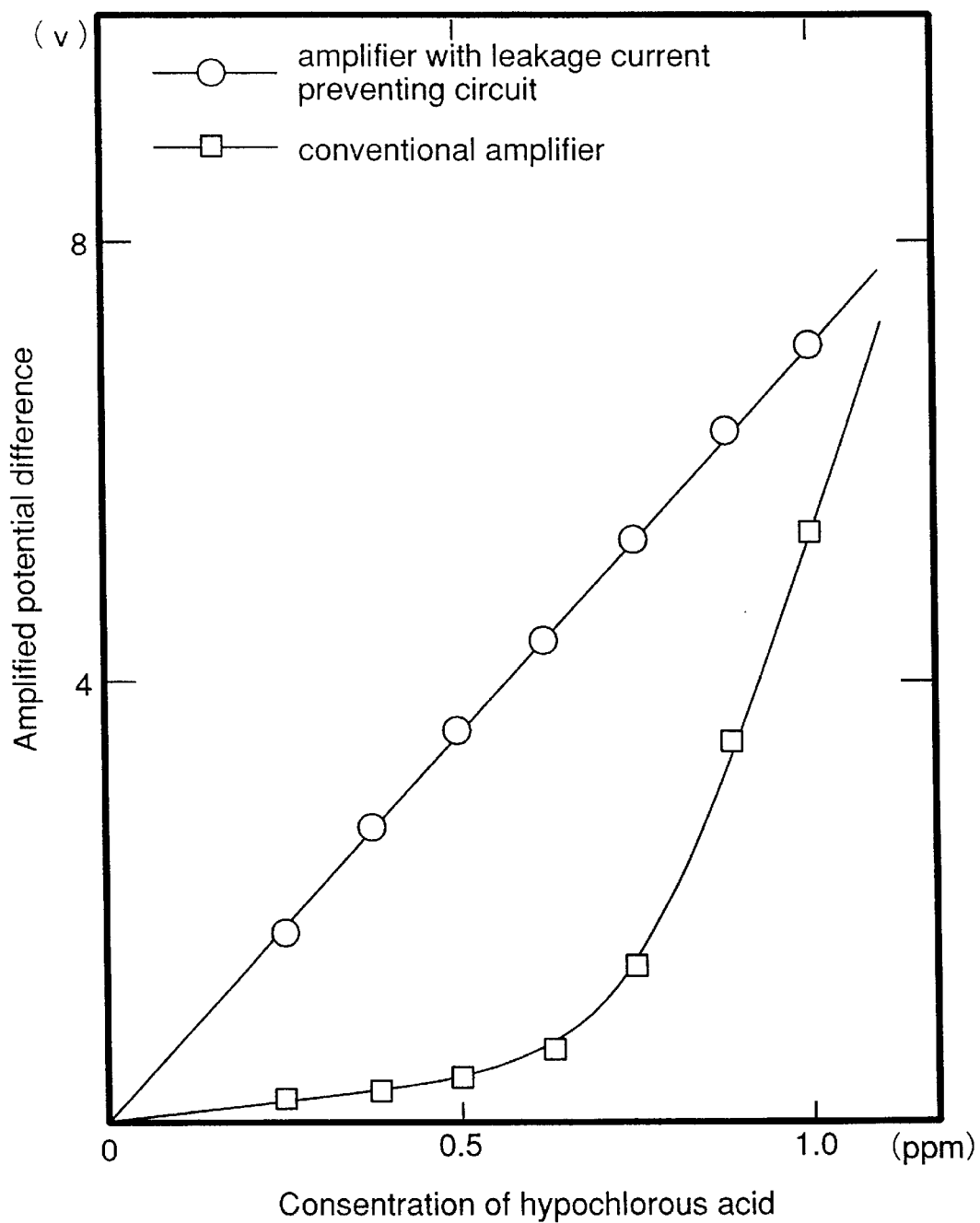
FIG. 7 is a graph comparing the amplified state of a measured potential difference amplified by the amplifier having the leakage current preventing circuit of the embodiment 1 of the present invention and that amplified by the conventional amplifier.

FIG. 7 shows a result of comparison of a case in which the amplifier 32 shown in FIG. 5 is used with a case that the conventional amplifier 32' is used as to the relationship between the amplified potential difference and the concentration of free hypochlorous acid.

As shown in FIG. 7, in the conventional amplifier 32' without the leakage current preventing circuit unit 34, the potential difference cannot be correctly measured when the concentration of the hypohalogenous (chlorous) acid used in the 24-hour-operating bath of the embodiment 1 is in region of about 1 ppm or less. This is because that the measured potential difference which is amplified and outputted is lowered by being greatly affected by the leakage current Ib from an amplifying transistor TR even if the value of it is very small and only 30 pA. However, the effect of the leakage voltage can be eliminated by the provision of the leakage current preventing circuit unit 34 and a correct potential difference proportional to the concentration of hypohalogenous acid can be amplified and outputted, whereby the potential difference resulting from the hypohalogenous acid having a low concentration can be correctly measured.

(Embodiment 2)

Figure 8:
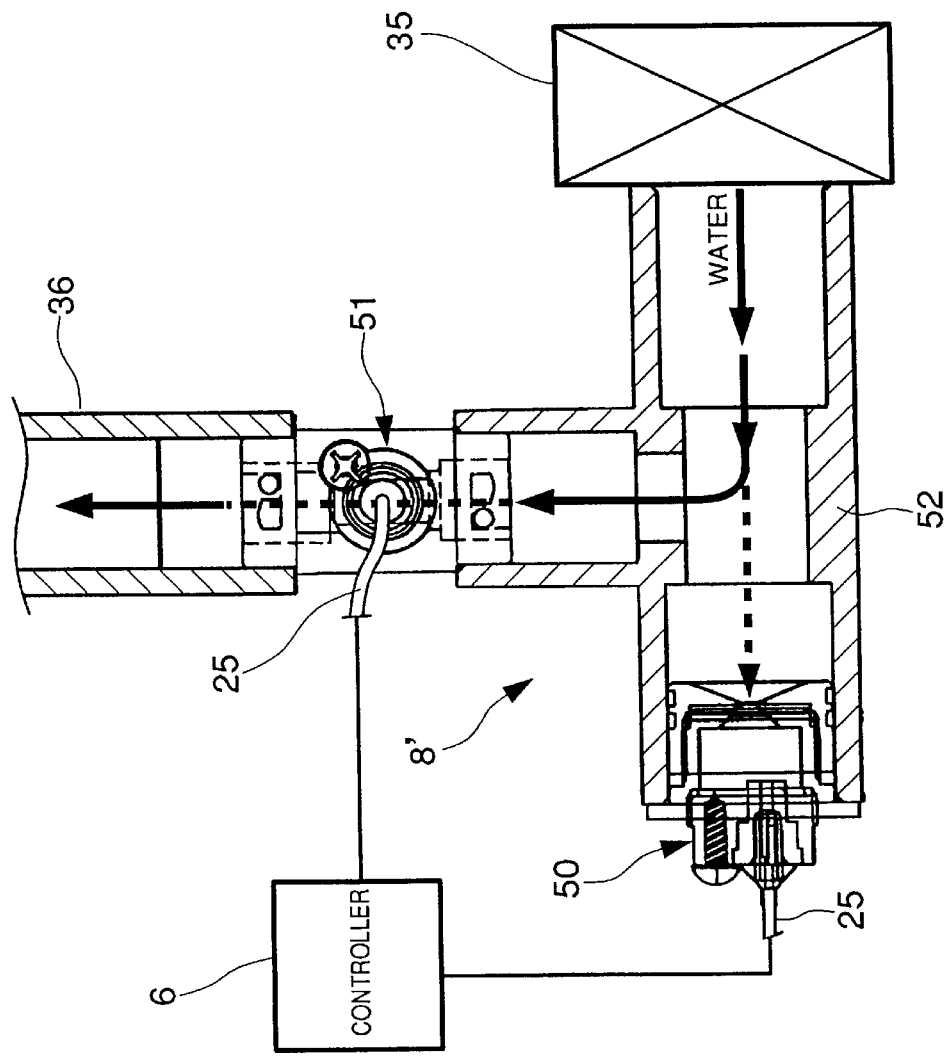
FIG. 8 is a side sectional view showing a sensor unit used in an embodiment 2 of the present invention.
Figure 9:
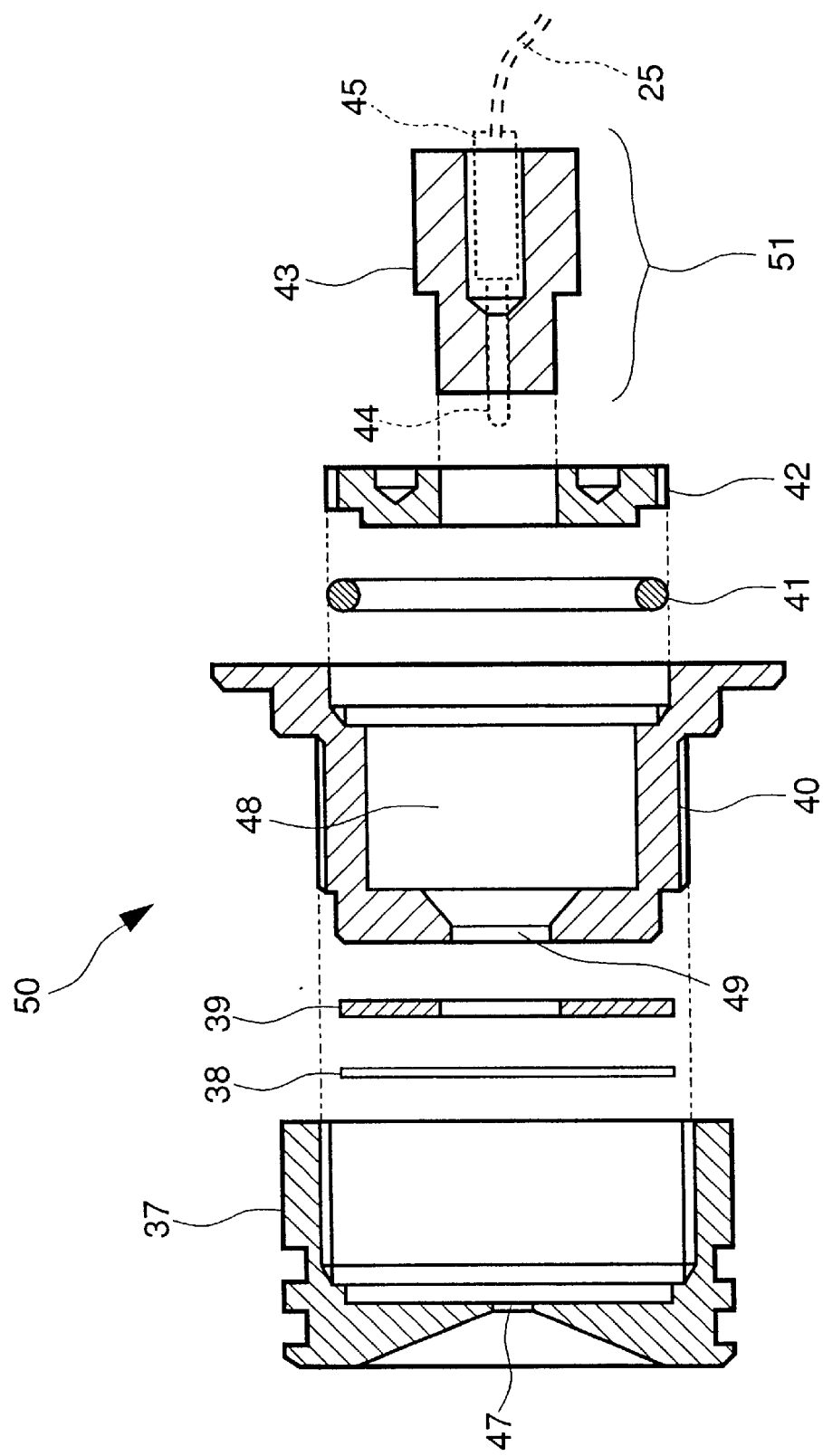
FIG. 9 is an exploded sectional view showing the structure of a reference electrode unit used in the embodiment 2 of the present invention.

FIG. 8 is a side sectional view showing a sensor 8' of an embodiment 2 and FIG. 9 is an exploded perspective view showing a reference electrode unit 50 of the embodiment 2.

The embodiment 2 has the sensor 8' shown in FIG. 9 mounted thereon in place of the sensor unit 8 of the embodiment 1 and the other arrangement of the embodiment 2 is the same as that of the embodiment 1.

As shown in FIG. 8, the sensor 8' of the embodiment 2 is arranged such that the reference electrode unit 50 is disposed to an end of a T-shaped port 52, the water in an auxiliary flow area 36 flows into the reference electrode unit 50 and the passage of the water is changed by the T-shaped port 52 so that it flows out to the other end of the T-shaped port 52 where a measuring electrode unit 51 is disposed.

The reference electrode unit 50 of the embodiment 2 is arranged as shown in FIG. 9. That is, the reference electrode unit 50 is composed of a lid member 37 having a prescribed opening 47 which is formed at the center thereof and in which an ion exchange membrane 38 can be disposed, an O-ring 39 for fixing the ion exchange membrane 38, a reference electrode vessel 40 which is engaged with the lid member 37 through the thread section formed to the outside periphery thereof and fixes the O-ring 39 and the ion exchange membrane 38 by clamping them between the extreme end thereof and the lid member 37 as well as has a reference electrode chamber 48 formed in the interior thereof, an approximately cylindrical electrode carrier 43 which carries a platinum electrode 44 therein and an electrode mounting lid 42 which is bonded to the electrode carrier 43 and attached to the reference electrode vessel 40 through a packing 41 to close the reference electrode chamber 48.

The platinum electrode 44 carried by the electrode carrier 43 is disposed in a state that it is exposed to the reference electrode chamber 48 and surrounded thereby. The opening 49 of the reference electrode chamber 48 is closed by the ion exchange membrane 38 so that the reference electrode chamber 48 is separated from the water in the auxiliary flow area 36 which communicates with the lid member 37 through the opening 47 formed thereto. As a result, the hypohalogenous (chlorous) acid contained in the water is decomposed by the ion exchange membrane 38 closing the reference electrode chamber 48 so that the interior of the reference electrode chamber 48 is maintained in a state that no hypochlorous (chlorine) acid exists therein.

Although the ion exchange membrane 38 is interposed between the reference electrode chamber 48 and the water in the embodiment 2 as described above, the present invention is not limited thereto and the ion exchange membrane 38 may be replaced with a membrane by which a catalyst capable of decomposing hypohalogenous (chlorous) acid is carried such as the nickel oxide and the oxide of iron, cobalt, titanium, manganese, etc. and activated carbon, etc. which are exemplified in the embodiment 1.

In the embodiment 2, the approximately cylindrical electrode carrier 43 as a simple body, which carries therein the platinum electrode 44 connected to a measuring cable 25 through a crimp-style terminal 45, is disposed as shown in FIG. 9 and used as the measuring electrode unit 51.

It is preferable that the platinum electrode 44 is connected to the measuring cable 25 through the crimp-style terminal 45 in such a manner that the copper wires or the like of the measuring cable 25 come into direct contact with the platinum electrode 44.

In the embodiment 2, the interior of the reference electrode chamber 48 is filled with a potassium chloride aqueous solution having a concentration set to 2 wt %.

When the concentration of the potassium chloride aqueous solution filled in the reference electrode chamber 48 is too high, the potential difference obtained when the potassium chloride aqueous solution begins to be used with hypohalogenous acid having a prescribed concentration is gradually dropped as the aqueous solution is used because potassium ion is dispersed through the ion exchange membrane 38; whereas when the concentration of the potassium chloride aqueous solution is too low, the potential difference cannot be preferably detected through the hypohalogenous acid. Accordingly, it is preferable that the potassium chloride aqueous solution has such a concentration as not to change the potential difference for a long period and the concentration is within the range of 0.5–10 wt % and preferably within the range of 1–3 wt %, although the concentration somewhat changes depending upon the concentration of salt in the water, and the like.

Figure 10:
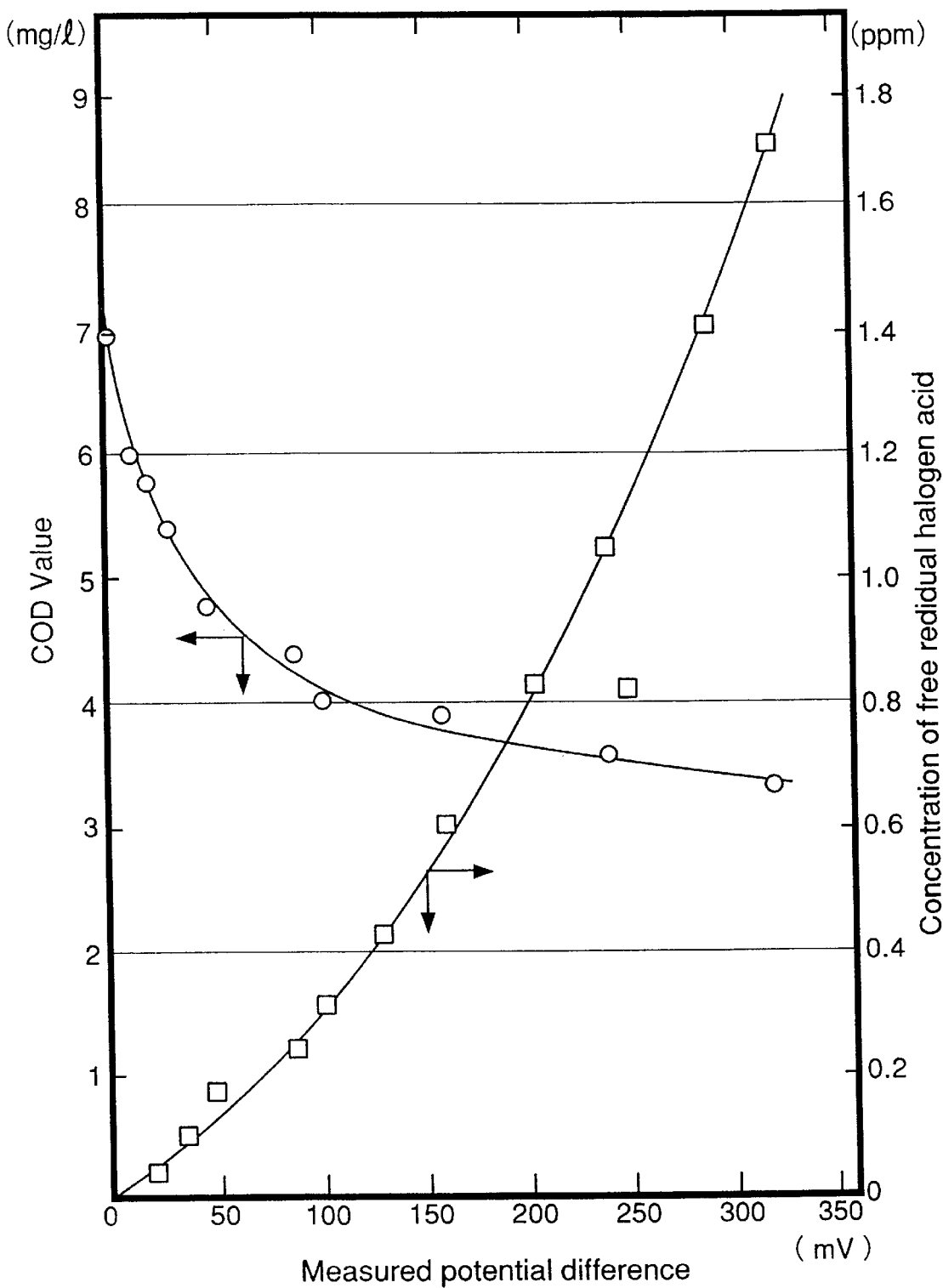
FIG. 10 is a graph showing the relationship among a COD value and a free residual halogen acid concentration at the sensor of the embodiment 2 of the present invention and a measured potential.

FIG. 10 shows the result of measurement of the relationship among the potential difference caused between the measuring electrode 51 and the reference electrode 50, the COD value of the water and the concentration of free residual halogen (chloric) acid when bathing is suitably taken likewise the embodiment 1 using the sensor 8' of the second embodiment.

As shown in FIG. 10, since a correlation is established among the concentration of free residual halogen (chloric) acid, the COD value and the measured potential difference likewise the embodiment 1, a polluted state of water and the COD value as the index of pollution at the time can be determined by measuring the potential difference of the water.

Figure 11:
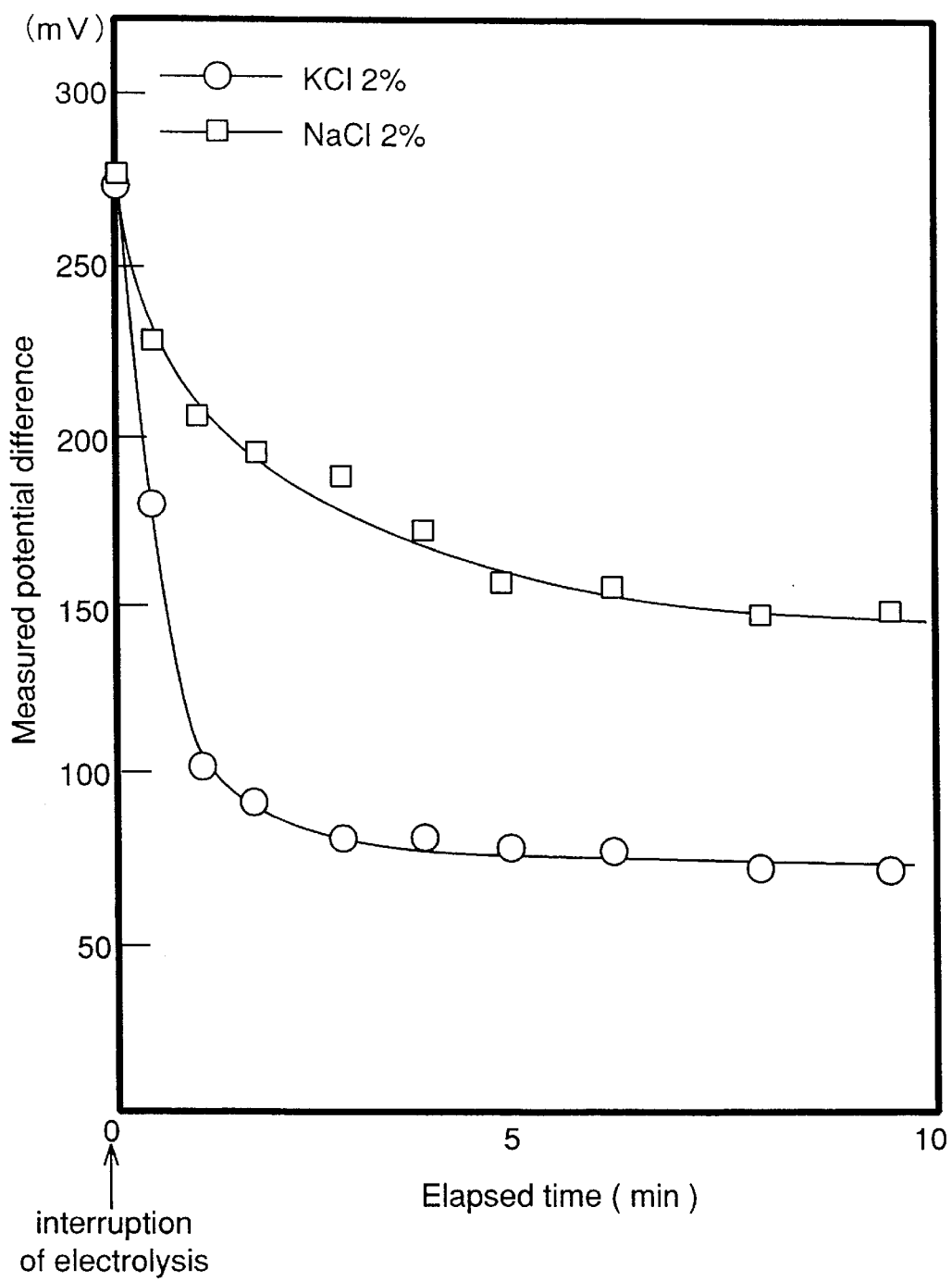
FIG. 11 is a graph showing a potential difference converging speed after the completion of electrolysis when a reference electrode chamber of the embodiment 2 of the present invention is filled with an aqueous solution containing potassium ion and sodium ion.

The converging speeds of the potential difference after electrolysis was stopped were compared as to a case that the reference electrode chamber 48 was filled with a sodium chloride aqueous solution of 2 w % and a case that it was filled with the above potassium chloride aqueous solution of 2 w % and FIG. 11 shows the result of comparison.

As shown in FIG. 11, when electrolysis is carried out by energizing an electrolyzer 4, a slight amount of charge is accumulated in the water and the measuring electrode is affected thereby. As a result, there is a tendency that a potential difference indicating a concentration higher than the actual concentration of free residual halogen (chloric) acid is detected. To cope with this problem, the embodiment reduces the effect of the noise due to the electrolysis by measuring the potential difference after a prescribed time having been preset elapses. It can be found that the converging speed of the potential difference increased by the electrolysis is higher when the reference electrode chamber 48 is filled with the potassium chloride aqueous solution and accordingly the potential difference can be measured at earlier timing.

A reason why the increased potential difference can be more promptly converged by potassium ion than sodium ion is as described below. That is, although the hydration power of ion with water is in the order of lithium>sodium>potassium due to the ionic radius thereof, the moving speed of each ion in water is in the order of lithium<sodium<potassium because ion having smaller hydration power has a higher speed. More specifically, it can be conceived that since potassium ion has a higher moving speed, the effect of the charge in water on the measuring electrode can be more promptly eliminated.

It is preferable to measure the potential difference at earlier timing because the intervals between the interruption of the electrolysis and the restart thereof can be shortened by it.

While the present invention has been described above with reference to the accompanying drawings, the present invention is by no means limited to the above embodiments and it goes without saying that modifications and additions can be made within the range which does not depart from the gist of the invention.

Although the respective embodiments have described the example that the water pollution evaluating mechanism of the present invention is applied to the 24-hour-operating bath, the present invention is not limited to the 24-hour-operating bath and it is needless to say that the evaluation mechanism can evaluate the pollution of the water used in a pool, fish raising vessel, cooling tower and the like in addition to the 24-hour-operating bath.

Since the description has been made as to the 24-hour-operating bath in the above embodiments, hypochlorous acid is mainly described as hypohalogenous acid having a sterilizing capability. In the present invention, however, the hypohalogenous acid may be hypobromous acid and it goes without saying that the pollution of water can be evaluated even by the hypobromous acid because the hypobromous acid can produce a potential difference matched to the concentration thereof likewise the hypochlorous acid.

Although the leakage current of the amplifying transistor TR is cancelled by the use of the P- and N-channel J-FETs in the above embodiments, the present invention is not limited thereto and the leakage voltage can be lowered or cancelled by using the leakage current preventing circuit arranged differently.

Further, although the embodiments use the catalyst and the ion exchange membrane individually, the present invention is not limited thereto and the hypohalogenous acid may be decomposed by using them in combination.

The present invention achieves the following advantages.

(a) According to a first aspect of the invention, there is established such a correlation that when the COD component as the polluted component in the water increases, the hypochlorous acid and hypobromous acid produced in the electrolyzer to sterilize and purify the COD component is consumed and the potential difference caused between the respective electrodes drops, whereas when the COD component as the polluted component in the water decreases, the hypochlorous acid and hypobromous acid are not consumed and the potential difference caused between the respective electrodes increases. Accordingly, the measurement of the potential difference permits the COD value of the water at the time to be simply evaluated at an almost real time.

(b) According to a second aspect of the invention, since the difference between the water into which the reference electrode is dipped and the water into which the measuring electrode is dipped resides only in the concentration of the hypochlorous acid and/or the hypobromous acid and the waters contain almost the same other electrolyte components, the potential difference resulting from the difference of concentrations of the other electrolyte components can be almost eliminated. Therefore, the potential difference based on the difference of the concentrations of the hypochlorous acid and/or the hypobromous acid can be correctly measured.

(c) According to a third aspect of the invention, since the pollution level or the COD value based on the potential difference is automatically converted by the conversion unit and output, the pollution level or the COD value of the water at the time can be directly confirmed when necessary.

(d) According to a fourth aspect of the invention, since the water flows through the auxiliary flow area in an approximately constant flow rate regardless of the fluctuation of the flow rate of the water in the main flow passage caused by the respective states of sterilization and purification, the change of the measured potential difference due to the fluctuation of the flow rate. Accordingly, the potential difference can stably be measured regardless of the state of the main flow passage.

(e) According to a fifth aspect of the invention, the effect of the charge accumulated in the water by the electrolysis on the measured potential difference can be reduced, whereby the potential difference can be more correctly measured.

(f) According to a sixth aspect of the invention, since not only the interior of the reference electrode chamber can be simply made to a state in which neither hypochlorous acid nor hypobromous acid exists by the use of the membrane-like decomposing unit but also the reference electrode chamber can be closed by the decomposing means, only the hypochlorous acid and hypobromous acid which intend to invade into the reference electrode chamber is decomposed. Accordingly, the amount of hypochlorous acid and hypobromous acid to be decomposed by the decomposing unit can be reduced, whereby the life of the decomposing unit can be prolonged.

(g) According to a seventh aspect of the invention, since potassium ion exists in the reference electrode chamber and the moving speed of the potassium ion is higher than that of other alkaline ions such as sodium ion, lithium ion, etc., the potassium ion increases a property for following the change of the potential difference, whereby the sensitivity in the measurement of the potential difference can be increased as well as the effect of the electrolysis on the measurement of the potential difference can be promptly eliminated to thereby shorten a measuring time.

(h) According to an eighth aspect of the invention, even if hypochlorous acid or hypobromous acid of a relatively low concentration is used in the pool, bath, cooling tower, fish raising vessel and the like, the effect of the leakage current on the small potential difference caused between the electrodes can be reduced or eliminated and the potential difference is correctly amplified. Accordingly, the potential difference can be correctly measured as well as even if the concentration of the hypochlorous acid and hypobromous acid is relatively low, the COD value can be correctly evaluated.

(i) According to a ninth aspect of the invention, the concentration, flow rate and the like of the hypochlorous acid and hypobromous acid can be simply controlled based on the COD values of the water in correspondence to the respective pollution levels because the pollution levels which correspond to the COD values are outputted.

What is claimed is:

1. A water pollution evaluating system comprising:
   a reservoir holding a body of water;
   means for supplying to said body of water a halogen ion;
   an electrolyzer for electrolyzing said water;
   means for circulating water from said reservoir to and through said electrolyzer to produce hypohalogenous acid in said circulating water to sterilize and purify the body of water;
   a measuring electrode dipped into the circulating water containing the hypohalogenous acid;
   a reference electrode dipped into a portion of the circulating water, and means for eliminating from the water in contact with the reference electrode substantially all hypohalogenous acid;
   potential difference measuring means communicating with said measuring electrode and said reference electrode to measure the potential difference between the water containing hypohalogenous acid and the water free of hypohalogenous acid; and
   means for evaluating the measured potential difference as a COD value to indicate a level of pollution.

2. A water pollution evaluating system according to claim 1, further comprising:
   conversion means for converting the potential difference into a pollution level set to a prescribed grade or a COD value; and
   output means for outputting the converted pollution level or the COD value.

3. A water pollution evaluating system according to claim 1, further comprising an auxiliary flow area which is branched from a main flow passage of the circulating water and through which a portion of the water passes in an approximately constant flow rate, wherein at least said reference electrode is disposed to said auxiliary flow area.

4. A water pollution evaluating system according to claim 1, further comprising time measuring means for starting the measurement of time when the electrolysis carried out by said electrolyzer is interrupted, wherein the potential difference is measured when a preset time elapses from the start of the measurement of the time.

5. A water pollution evaluating system according to claim 1, further comprising:
   a reference electrode chamber surrounding said reference electrode and communicating with the water; and
   membrane-like decomposing means selected from at least one of following types a membrane carrying a catalyst and activated carbon, capable of decomposing hypochlorous acid and hypobromous acid, and an ion exchange membrane disposed to close said reference electrode chamber.

6. A water pollution evaluating system according to claim 5, wherein the interior of said reference electrode chamber is filled with water containing potassium ion having a prescribed concentration.

7. A water pollution evaluating system according to claim 1, wherein said potential difference measuring means includes a leakage current preventing circuit disposed in front of an amplifier for amplifying the potential difference caused between said respective electrodes for canceling or reducing the leakage voltage from the amplifier.

8. A water pollution evaluating system according to claim 1, wherein said potential difference measuring means sets a pollution level to each COD level in a prescribed range and outputs a pollution level corresponding to a COD value evaluated based on a measured potential difference.

9. A water pollution evaluating system according to claim 1, wherein said reference electrode is dipped into the same water as that into which said measuring electrode is dipped except that the hypochlorous acid and/or hypobromous acid contained in the water into which said reference electrode is dipped is substantially decomposed.

10. A water pollution evaluating system according to claim 1, wherein said reservoir is a pool, a bath, a cooling tower, or a fish raising vessel.

11. A water pollution evaluating system according to claim 1, wherein said halogen is a chlorine ion and/or a bromine ion.

12. A water pollution evaluating system according to claim 1, wherein said hypohalogenous acid is a hypochlorous acid and/or a hypobromous acid.

13. A process for evaluating pollution in a body of water stored in a reservoir comprising the steps of:
   supplying to said body of water a halogen ion;
   electrolyzing said water by circulating water from said reservoir to and through an electrolyzer to produce hypohalogenous acid in said circulating water to sterilize and purify the body of water;
   circulating water containing the hypohalogenous acid in contact with a measuring electrode;
   circulating water in contact with a reference electrode;
   eliminating from the water in contact with the reference electrode substantially all hypohalogenous acid;
   measuring the potential difference between the water containing hypohalogenous acid and the water free of hypohalogenous acid; and
   evaluating the measured potential difference as a COD value to indicate a level of pollution.

14. The process of claim 13, wherein said reservoir is a pool, a bath, a cooling tower, or a fish raising vessel.

15. The process of claim 13, wherein said halogen is a chlorine ion and/or a bromine ion.

16. The process of claim 13, wherein said hypohalogenous acid is a hypochlorous acid and/or a hypobromous acid.

* * * * *

UNITED STATES PATENT AND TRADEMARK OFFICE
CERTIFICATE OF CORRECTION

PATENT NO. : 6,235,188 B1
DATED : May 22, 2001
INVENTOR(S) : Nakamura et al.

It is certified that error appears in the above-identified patent and that said Letters Patent is hereby corrected as shown below:

<u>Title page,</u>
Item [75], Inventor, "Osaka" should be -- Osaka-fu -- (both occurrences) and "Habikino" should be -- Osaka-fu -- (both occurrences).

<u>Column 14,</u>
Line 2, after "types" insert -- , -- (comma).

Signed and Sealed this

Fifth Day of November, 2002

*Attest:*

*Attesting Officer*

JAMES E. ROGAN
*Director of the United States Patent and Trademark Office*